(12) United States Patent
Unhoch et al.

(10) Patent No.: US 8,440,212 B2
(45) Date of Patent: May 14, 2013

(54) COMPOSITIONS FOR TREATING WATER SYSTEMS

(75) Inventors: Michael J. Unhoch, Tyrone, GA (US); Patricia Brown, Newark, DE (US)

(73) Assignee: Arch Chemicals, Inc., Atlanta, GA (US)

( * ) Notice: Subject to any disclaimer, the term of this patent is extended or adjusted under 35 U.S.C. 154(b) by 287 days.

(21) Appl. No.: 12/806,074

(22) Filed: Aug. 5, 2010

(65) Prior Publication Data

US 2011/0045977 A1 Feb. 24, 2011

Related U.S. Application Data

(60) Provisional application No. 61/274,995, filed on Aug. 24, 2009.

(51) Int. Cl.
| | |
|---|---|
| A01N 25/02 | (2006.01) |
| A01N 33/00 | (2006.01) |
| A01N 37/52 | (2006.01) |
| A01N 55/02 | (2006.01) |
| A01N 59/16 | (2006.01) |

(52) U.S. Cl.
USPC ........... 424/405; 424/617; 424/641; 504/150; 504/152; 504/158; 514/635

(58) Field of Classification Search .................... None
See application file for complete search history.

(56) References Cited

U.S. PATENT DOCUMENTS

| | | |
|---|---|---|
| 5,449,658 A | 9/1995 | Unhoch et al. |
| 6,710,017 B2 | 3/2004 | Unhoch et al. |
| 7,494,963 B2 | 2/2009 | Ahmed et al. |
| 7,501,027 B2 | 3/2009 | Ahmed et al. |
| 7,511,006 B2 | 3/2009 | Shimmin et al. |
| 7,537,776 B1 | 5/2009 | Beilfuss et al. |
| 7,560,421 B2 | 7/2009 | Nakada et al. |
| 7,569,212 B2 | 8/2009 | Wagenaar |
| 2007/0258915 A1 | 11/2007 | Kielbania |
| 2008/0142453 A1 | 6/2008 | Unhoch et al. |
| 2008/0258104 A1 | 10/2008 | Mullins et al. |
| 2008/0274208 A1 | 11/2008 | Unhoch et al. |

Primary Examiner — Neil Levy
(74) Attorney, Agent, or Firm — Lucas & Mercanti, LLP

(57) ABSTRACT

The present invention relates to treatment of water, and more specifically to treatment of water using a stable formulation of polyhexamethylene biguanide (PHMB) and a liquid or solid zinc salt for the application and prevention algae in recirculated and stagnant water systems. The invention also encompasses methods of treating water that already contains PHMB.

6 Claims, 2 Drawing Sheets

COMPOSITIONS FOR TREATING WATER SYSTEMS

CROSS-REFERENCE TO RELATED APPLICATIONS

This application claims the benefit of U.S. Provisional Patent Application Serial No. 61/274,995 filed Aug. 24, 2009. That application is incorporated by reference in its entirety herewith.

BACKGROUND OF THE INVENTION

1. Field of the Invention

The present invention relates to treatment of water, and more specifically to treatment of water using a stable formulation of polyhexamethylene biguanide (PHMB) and a liquid or solid zinc salt for the treatment and prevention algae in recirculated and stagnant water systems.

2. Brief Description of the Art

Polyhexamethylene biguanide (PHMB) is a known fast-acting and broad spectrum antimicrobial compound that is used in a variety of applications including eye and skin treatment compositions (U.S. Pat. Nos. 7,569,212; 7,560,421), cleaning compositions (U.S. Pat. Nos. 7,511,006; 7,501,027; 7,494,963), preservatives (U.S. Pat. No. 7,537,776), and as a treatment (sanitizer) for water systems (U.S. Pat. No. 6,710,017). PHMB is used as a sanitizer or preservative to kill bacteria (including methicillin-resistant *Staphylococcus aureus* (MRSA), *Salmonella, Campylobacter*, and *E. coli*) and viruses, and to control algae in a wide range of applications, including preserving wet wipes; controlling odor in textiles; preventing microbial contamination in wound irrigation and sterile dressings; disinfecting medical/dental utensil and trays, farm equipment, animal drinking water, and hard surfaces for food handling institutions and hospitals; and to deodorize vacuums and toilets. PHMB is used in antimicrobial hand washes and rubs and air filter treatments as an alternative to ozone. As a preservative, PHMB is used in cosmetics, personal care products, fabric softeners, contact lens solutions, hand washes, and the like. For pool and spa applications, PHMB is sold under the tradename BAQUACIL by Arch Chemicals, Inc. (Norwalk, CT).

Organic algaecides are often added apart from a sanitizer either as part of a system combined with sanitizer and/or oxidizer to prevent algal contamination in swimming pools. The most effective algae preventative treatment is copper sulfate and/or chelated copper products.

However, PHMB reacts with copper to form an insoluble colored precipitate. Thus, copper products are incompatible with PHMB in both a formulated product and at levels used to prevent algae in swimming pools (e.g., 0-2 ppm). What is needed in the art is a composition of long-lasting algae preventative and PHMB that does not form precipitates, and is effective for preventing algal contamination in stagnant or recirculating water systems. The present invention is believed to be an answer to that need.

SUMMARY OF THE INVENTION

The invention is directed to compositions for treating recirculating or stagnant water, comprising polyhexamethylene biguanide (PHMB) and one or more zinc salts. The compositions preferably contain from 0.1 to 99.9 wt % PHMB and from 0.1 to 95 wt % of one or more zinc salts. It has been unexpectedly discovered that PHMB and zinc salts do not form insoluble precipitates and have been shown to be compatible in a formulation as well as in application without any impact on the zinc ions ability to prevent algae growth and the PHMB's ability to control bacteria.

The invention is also directed to a method of controlling algae in a body of recirculating or stagnant water, comprising the steps of (1) providing a body of recirculating or stagnant water containing PHMB; and (2) adding a zinc salt to a final zinc concentration ranging from 0.1 to 5 PPM.

BRIEF DESCRIPTION OF THE DRAWINGS

The invention will be better understood from the following detailed description and accompanying drawings, in which.

DETAILED DESCRIPTION OF THE INVENTION

Figure 1:
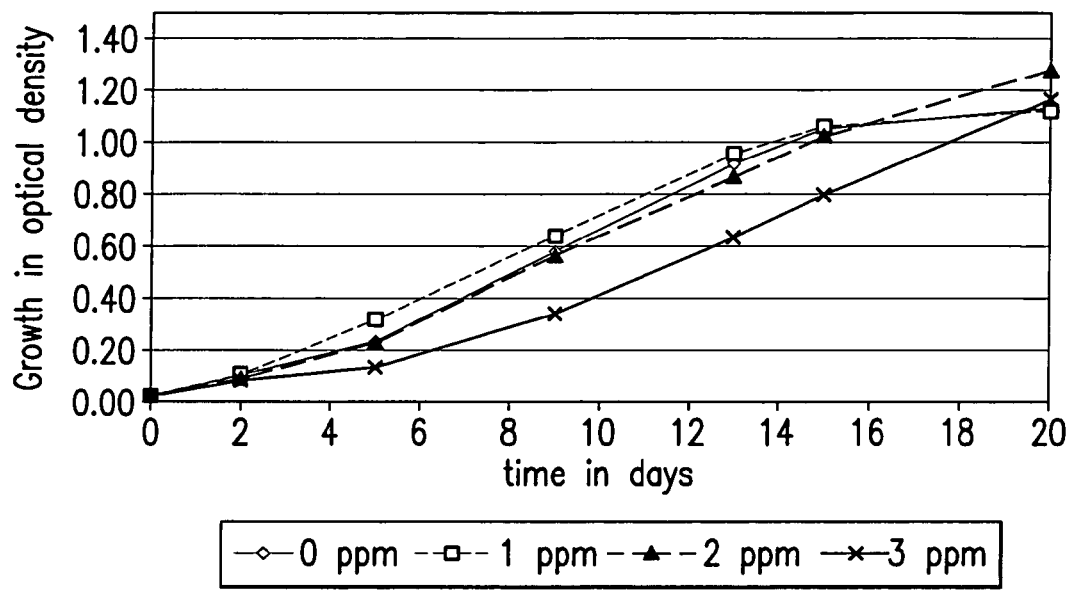
FIG. 1 is a graph showing the efficacy of zinc sulfate and PHMB against a strain of mustard algae.

PHMB is an effective sanitizer in recreational water, such as swimming pools and hot tubs, and acts as a chlorine-free polymeric sanitizer, which is effective against a wide variety of microorganisms, as disclosed in U.S. Pat. No. 6,710,017. PHMB is particularly advantageous for use in pools, hot tubs, and spas because it is not affected by sunlight, water temperature, or pH fluctuations. In addition, it retains activity in hard water and does not cause surface streaks or tackiness. PHMB is stable over a wide pH range (1-11), has low foaming properties, contains zero VOCs, and is formaldehyde free. This stability allows a pool to be properly maintained for longer periods, generally 7-14 days before additional PHMB is required.

Copper sulfate and related chelated copper compounds have been shown to be very effective in preventing the growth of algae in ponds, swimming pools, and reservoirs. The amounts required to induce an algaecidal effect are generally quite low, on the order of 1 part per million. However, when combined with PHMB, copper products form an undesirable precipitate in pool water. The present inventors have found that combinations of PHMB and zinc salts do not form precipitates in recreational water applications, and that such compositions still retain both algaecidal and bactericidal properties.

As indicated above, the invention is directed to compositions for treating recirculating or stagnant water, comprising polyhexamethylene biguanide (PHMB) and one or more zinc salts. Each of these components is described in more detail below.

Polyhexamethylene biguanide (PHMB) may be present in the composition in a solid, liquid, or solution form. Preferably, the amount of solid PHMB in the composition ranges from 0.1 to 99.9 wt %, more preferably from 5 to 98 wt %, and most preferably from 10 to 90 wt %, all wt percents being based on the total weight of the composition. When formulated as a liquid or solution, the amount of PHMB ranges from 1 to 40% by weight.

One or more water soluble zinc salts are also included in the composition to provide a source of zinc ions ($Zn^{2+}$). Suitable water soluble zinc salts include, but are not limited to, zinc sulfate monohydrate ($ZnSO_4 \cdot H_2O$), zinc sulfate heptahydrate ($ZnSO_4 \cdot 7H_2O$), zinc carbonate ($ZnCO_3$), zinc nitrate ($ZnNO_3)_2$), zinc borate, zinc hydroxide, zinc phosphate, as well as combinations of these. One preferred zinc salt is zinc sulfate. The amount of zinc salts in the composition preferably range from 0.1 to 95 wt % in solid form, more preferably from 1 to 30 wt %, and most preferably from 2 wt % to 25 wt %, with all weight percents being based on the total weight of the composition. When formulated as a liquid or solution, the amount of zinc salt ranges from 1 to 10% by weight.

The components of the composition of the invention are combined using conventional techniques and may be formed into powders, granules, suspensions, tablets, or briquettes. In use, 500 grams (made from, for example, 400 g PHMB and 100 g zinc salt) of the composition may be initially added to 10,000 gallons of pool water followed by weekly additions of 100 g per 10,000 gallons of pool water to maintain PHMB and zinc levels needed to achieve the desired result. The desired result can also be obtained by adding 100 g weekly additions of the solid or initial dose followed by weekly additions per 10,000 gallons. In one embodiment, the composition of the invention delivers 0.1 to 5 PPM final concentration of zinc ions, and preferably from 0.5 to 3.0 PPM final concentration of zinc ions. The composition of the invention also delivers from 0.1 to 40 PPM final concentration of PHMB, preferably from 5 to 20 PPM final concentration of PHMB, and more preferably from 6 to 15 PPM final concentration of PHMB initially, and 0.1 to 5 PPM final concentration of zinc ions, and preferably from 0.5 to 3 PPM final concentration of zinc ions.

Additionally, PHMB and zinc salt may be applied as an "initial dose" to establish initial PHMB and zinc ion residuals in the body of recreational water. Following an initial dose, daily or weekly doses of the composition may be added to act as a maintenance/preventative step to prevent further growth of microorganisms. In one embodiment, a sufficient amount of the "initial dose" composition is added to water to achieve a PHMB concentration of about 10 PPM, and a zinc ion concentration of between 0.2 and 2.0 PPM.

The invention also encompasses methods of controlling algae in a body of recirculating or stagnant water. Preferably, bodies of recirculating water already include PHMB at levels ranging up to about 20 PPM, and preferably from 2 to 15 PPM. In the method of the invention, zinc salts mentioned above are added to the water so that the levels of zinc ions preferably range from 0.1 to 5.0 PPM final concentration of zinc ions, and more preferably from 0.5 to 3 PPM final concentration of zinc ion. One useful amount of zinc ion is 1.5 PPM.

The compositions according to the present invention may also contain additives known in the water treatment art. These additives include but are not limited to pigments, dissolution rate modifiers, binders, water softeners, phosphate removers, corrosion inhibitors, dissolution rate modifiers, oxidizers (peroxysalts, percarbonates, persulfates, and perborates, peroxides), lubricants, color-containing salts, biocides, buffers, chelating agents, other algaecides, fungicides, sequestering agents, clarifiers, enzymes, dyes, thickeners, fragrances, surfactants, co-solvents, biodisperants, biopenetrants, sorbitan monostearate, sulfamic acid, tallowpropylamine diamine, cocopropylamine diamine, oleylpropylamine diamine, stearyldimethylbenzylammonium chloride, and combinations thereof. These additives may be pre-blended with any of the components of the composition, and are generally present in the composition of the invention in amounts ranging from 0.2 to 10 weight percent.

The composition and method of the present invention may be used in any recirculating water system where algae infestation could occur, for example swimming pools, spas, hot tubs, and decorative ponds. In use as a treatment for swimming pools, the composition of the invention is added to a swimming pool recirculating water system to achieve desired concentration ranges and demonstrates a synergistic effect between the ingredients. The following examples are meant to illustrate, but in no way limit the present invention.

EXAMPLES

Example 1:

Efficacy of Zinc Sulfate Against Mustard Algae

Figure 2:
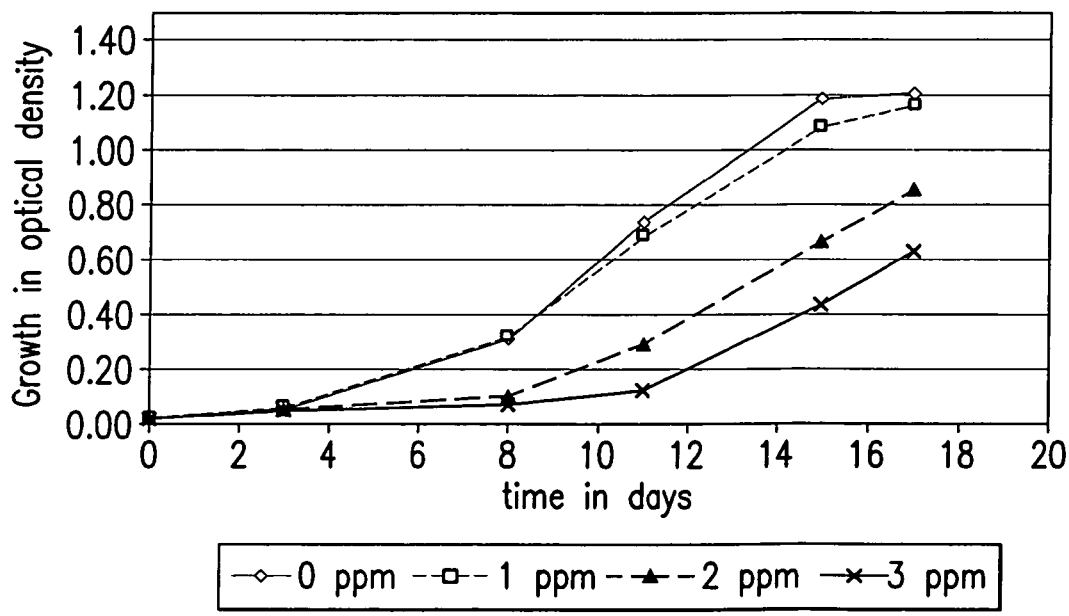
FIG. 2 is a graph showing the efficacy of zinc sulfate and PHMB against another strain of mustard algae.

Efficacy of zinc ions (in the form of zinc sulfate) was evaluated using two strains of very difficult to control wild mustard algae, both isolated from a pool treated with BAQUACIL (Arch Chemicals, Norwalk, CT). All experiments were conducted in 125 ml Erlenmeyer flasks that contained 50 ml of Jaworski's medium. To increase the surface area in the flasks each flask also contained 50 6 mm glass beads. The tests flasks were illuminated using a combination incandescent and fluorescent plant grow lights with 16 hours of illumination and 8 hours of darkness. Temperature was maintained at 80° F+/−5° F. The flasks were grown without agitation or additional aeration. One ml of a pooled mid-log culture was used to used to inoculate the test flasks to an initial optical density of 95%T. This yields an initial concentration of approximately 104 algae per ml. Efficacy was evaluated in the presence and absence of a sub-optimal concentration of a primary sanitizer (PHMB). Growth was measured optically at 450 nm using a 1 inch cell in a Spectronic 20. All experiments used five replicates. The results of the optical readings were arithmetically averaged. The results for combinations of PHMB and zinc sulfate are shown in FIG. 1 (Schwab strain) and FIG. 2 (Miami strain). In FIGS. 1 and 2, PHMB concentrations were held at 4 PPM, and zinc ion concentration was varied from 0 to 3 PPM. Growth over time was measured and plotted.

As shown in FIGS. 1 and 2, zinc ions exhibited moderate algaestatic activity against the two algae strains. The growth curves display classic dose response patterns. A concentration of 2 or 3 ppm zinc ions reduced the algal growth by approximately 50%. These results show that the PHMB does not interfere with the zinc ion activity against the algae; thus, showing the compatibility of the components at application levels in a swimming pool.

Example 2:

PHMB and Zinc Sulfate Formulation Compatibility

Two levels of zinc sulfate (2.5% and 5.0% by weight) were formulated with 20% by weight PHMB and stored for 3 weeks at room temperature and 54.5° C. This accelerated storage temperature shows the compatibility and shelf life stability of the PHMB when formulated with the zinc sulfate. The PHMB concentrations were tested initially and at one week intervals for three weeks. The data has been plotted at room temperature and at 54.5° C. and shown in FIG. 3.

Figure 3:
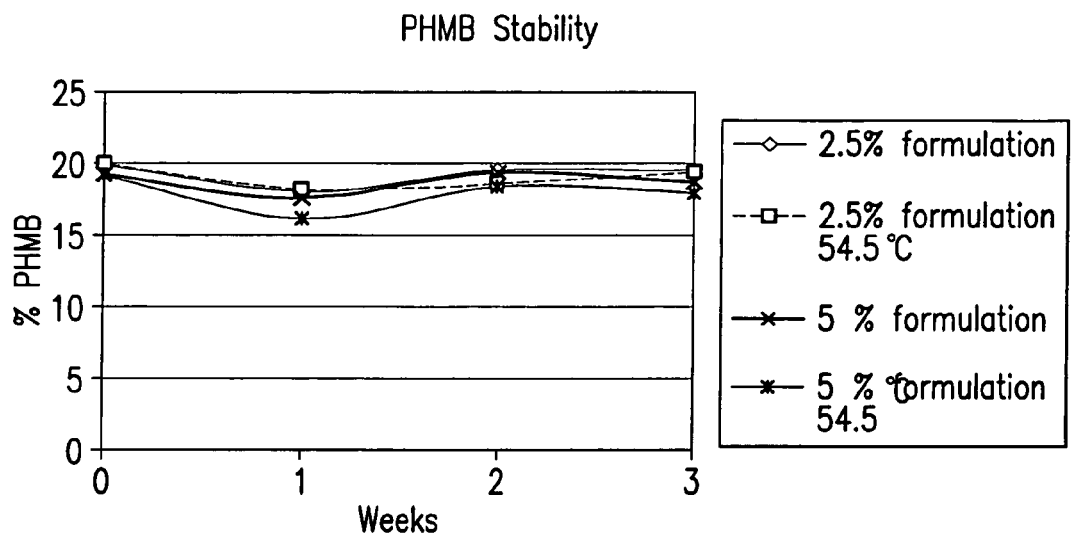
FIG. 3 is a graph showing storage stability of PHMB formulated with zinc sulfate.

FIG. 3 show that each formulation was stable at both room and accelerated (elevated) temperatures. This was unexpected because of the incompatibility of copper and other metal salts with PHMB even at use concentrations in the swimming pool.

Example 3:

Evaluation of New Preventative Treatments in Test Pools

This study was conducted in test pools without bathers. The water was initially balanced and proper water balance was maintained throughout the study. Each pool was inoculated weekly with mixed bacterial, fungal and algal cultures. The algae inoculations were prepared using the methodology below.

Algal cultures were maintained in 5 liter carboys at 22° C. under fluorescent light with a 12 hour on/off cycle. Air is continuously bubbled through the medium. Stock cultures of Chlorella *pyrenoidosa* and *Pleurochloris pyrenoidosa* are maintained in Kratz & Meyers medium and *Phormidium* sp., a filamentous blue-green alga, is maintained in BG-11.

150 milliliters of a combined inoculum containing equal amounts of each strain is added weekly per 10,000 gallons of water. Typically the cultures contain approximately $2 \times 10^7$ cells per milliliter; therefore approximately $2 \times 10^9$ cells are added per pool each week. However, if time allows, determine the actual number of algae in each sample by heamocytometry, using a Neubauer heamocytometer. Each pool was chemically treated using the procedure below.

A. Test Pool 7: Baquacil CDX +Didecyl dimethyl ammonium chloride (DDAC)

1. An initial Baquacil Sanitizer dose of 50 ppm (96 oz/ 10,000 gallons of pool water) was added, followed by weekly doses of Baquacil Sanitizer in order to maintain the level at or above 30 ppm (for example 16 oz of Sanitizer will raise the level about 12.5 ppm in a 10,000 gallon swimming pool).
2. The pool received an initial Baquacil oxidizer dose of 100 ppm (1 gallon/10,000 gallons of pool water), then weekly Baquacil Oxidizer doses of 25 ppm (1 quart).
3. Baquacil CDX was added at an initial concentration of 12 ppm (i.e.16 oz.), followed by weekly additions of 3 ppm Baquacil CDX (i.e. 4 oz)
4. A 225 ml initial dose of Bardac 2250 was added, followed by weekly dose of 75 ml After 102 days this pool received a single 4.2 ppm dosage of zinc sulfate (1.5 PPM zinc).

B. Test Pool 8: Baquacil CDX Control

1. An initial Baquacil Sanitizer dose of 50 ppm (96 oz/ 10,000 gallons of pool water) was added, followed by weekly doses of Baquacil Sanitizer in order to maintain the level at or above 30 ppm (for example 16 oz of Sanitizer will raise the level about 12.5 ppm in a 10,000 gallon swimming pool).
2. The pool received an initial Baquacil Oxidizer dose of 100 ppm (1 gallon/10,000 gallons of pool water), then weekly Baquacil Oxidizer doses of 25 ppm (1 quart).
3. Baquacil CDX was added at an initial concentration of 12 ppm (i.e.16 oz.), followed by weekly additions of 3 ppm Baquacil CDX (i.e. 4 oz)

After 33, 40 and 61 days of the study the pool received 4.2 ppm dosages of zinc sulfate (1.5 PPM zinc). The first was planned; the second two were inadvertent. No additional dosages were made for the remainder of the study.

Visual Algae Observations

Observations were taken on a business daily basis and the pool was scored using the following 0-4 scale.

Figure 4:
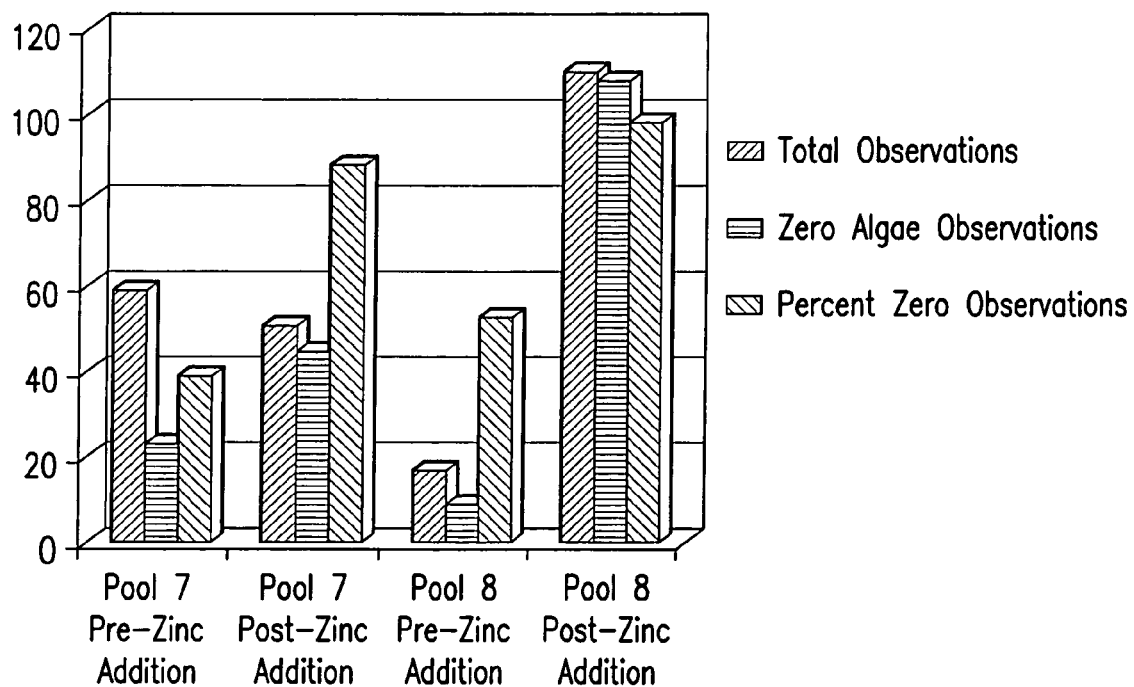
FIG. 4 is a graph showing algae observations in pools containing various combinations of PHMB and zinc sulfate.

0=no trace of algae
1=trace amounts
2=small patches
3=large patches
4=sides and bottom more than 25% covered by algae A compilation of the results were plotted and are shown in FIG. 4. As shown in FIG. 4, the data in the above demonstrates the improved algaestatic performance of both Pools 7 and 8 after the zinc sulfate additions.

While the invention has been described above with reference to specific embodiments thereof, it is apparent that many changes, modifications, and variations can be made without departing from the inventive concept disclosed herein. Accordingly, it is intended to embrace all such changes, modifications, and variations that fall within the spirit and broad scope of the appended claims. All patent applications, patents, and other publications cited herein are incorporated by reference in their entireties.

What is claimed is:

1. A method of controlling algae in a body of recirculating or stagnant water, comprising the steps of:
   providing a body of recirculating or stagnant water containing polyhexamethylene biguanide (PHMB); and
   adding a zinc salt.

2. The method of claim 1, wherein said zinc salt is selected from the group consisting of zinc sulfate monohydrate ($ZnSO_4.H_2$), zinc sulfate heptahydrate ($ZnSO_4.7H_2O$), zinc carbonate ($ZnCO_3$), zinc nitrate ($Zn(NO_3)_2$), zinc borate, zinc hydroxide, zinc phosphate, and combinations thereof.

3. The method of claim 1, wherein said adding step comprises adding said zinc salt to establish a final concentration of zinc ion of between 0.1 and 5 PPM.

4. The method of claim 1, wherein said adding step comprises adding said zinc salt to establish a final concentration of zinc ion of between 0.5 and 3.0 PPM.

5. The method of claim 1, wherein said PHMB is present in said body of recirculating or stagnant water in a concentration of up to 20 PPM.

6. The method of claim 5, wherein said PHMB concentration ranges from 2 to 15 PPM.

* * * * *

UNITED STATES PATENT AND TRADEMARK OFFICE
CERTIFICATE OF CORRECTION

PATENT NO. : 8,440,212 B2
APPLICATION NO. : 12/806074
DATED : May 14, 2013
INVENTOR(S) : Michael J. Unhoch et al.

It is certified that error appears in the above-identified patent and that said Letters Patent is hereby corrected as shown below:

In the Claims

Column 6, line 37 in claim 2,
"$ZnSO_4 \cdot H2$" should read -- $ZnSO_4 \cdot H_2O$ --

Signed and Sealed this
Twenty-sixth Day of November, 2013

Margaret A. Focarino
*Commissioner for Patents of the United States Patent and Trademark Office*